(12) United States Patent
Moloney et al.

(10) Patent No.: US 6,930,118 B2
(45) Date of Patent: Aug. 16, 2005

(54) 3-OXADIAZOL-5-YL-1-AMINOALKYL-1H-INDOLE DERIVATIVES

(75) Inventors: Peter Gerard Moloney, West Brunswick (AU); Alan Duncan Robertson, South Melbourne (AU)

(73) Assignee: Amrad Operations Pty. Ltd., Richmond (AU)

( * ) Notice: Subject to any disclaimer, the term of this patent is extended or adjusted under 35 U.S.C. 154(b) by 0 days.

(21) Appl. No.: 10/399,622

(22) PCT Filed: Nov. 2, 2001

(86) PCT No.: PCT/AU01/01417

§ 371 (c)(1),
(2), (4) Date: Aug. 22, 2003

(87) PCT Pub. No.: WO02/36590

PCT Pub. Date: May 10, 2002

(65) Prior Publication Data

US 2004/0034073 A1 Feb. 19, 2004

(51) Int. Cl.⁷ .................. A61K 31/4245; C07D 413/14; C07D 417/14
(52) U.S. Cl. ...................... 514/364; 548/131; 546/196; 544/62; 544/367
(58) Field of Search ......................... 514/364; 548/131

(56) References Cited

U.S. PATENT DOCUMENTS

| | | | |
|---|---|---|---|
| 4,939,138 A | 7/1990 | D'Ambra et al. | 514/218 |
| 4,973,587 A | 11/1990 | Ward et al. | 514/235.2 |
| 5,013,837 A | 5/1991 | Ward et al. | 544/143 |
| 5,068,234 A | 11/1991 | D'Ambra et al. | 514/235.2 |
| 5,998,409 A | 12/1999 | Gaster et al. | 514/230.02 |
| 6,013,648 A | 1/2000 | Rinaldi et al. | 514/235.2 |

FOREIGN PATENT DOCUMENTS

| | | |
|---|---|---|
| EP | 0 328 200 A1 | 8/1989 |
| WO | WO 93/02677 | 2/1993 |
| WO | WO 96/25397 | 8/1996 |

OTHER PUBLICATIONS

Kelarev et al., Zhurnal Organicheskoi Khimii (1993), 29(4), pp. 763–769.*
Kelarev et al., Khimicheskaya Tecknologiya (1993), 36(3), pp. 49–55.*
Chemical Abstracts 120:270260, 1994.
Chemical Abstracts 120:77192, 1994.
D'Ambra, T. et al., "Conformationally Restrained Analogues of Pravodoline: Nanomolar Potent, Enantioselective, (Aminoalkyl) Indole Agonists of the Cannabinoid Receptor," *J. Med. Chem.* 35:124–135, 1992.
D'Ambra, T. et al., "C–Attached Aminoalkylindoles: Potent Cannabinoid Mimetics," *Bioorganic & Medicinal Chemistry Letters* 6(1):17–22, 1996.
Di Marzo, V. et al., "The Endogenous Cannabinoid Signalling System: Chemistry, Biochemistry and Physiology," *Internet Journal of Science—Biological Chemistry*, Feb. 1997.
Dutta, A. et al., "Synthesis, Pharmacology, and Molecular Modeling of Novel 4–Alkyloxy Indole Derivatives Related to Cannabimimetic Aminoalkyl Indoles (AAIs)," *Bioorganic and Medicinal Chemistry* 5(8):1591–1600, 1997.
Eissenstat, M. et al., "Aminoalkylindoles: Structure—Activity Relationship of Novel Cannabinoid Mimetics," *J. Med. Chem.* 38:3094–3105, 1995.
Hanus, L. et al., "HU–308: A Specific Agonist for CB2, a Peripheral Cannabinoid Receptor," *Proc. Natl. Acad. Sci. USA* 96(25):14228–14233, Dec. 1999.
Swain, C. et al., "Novel 5–HT3 Antagonists. Indole Oxadiazoles," *J. Med. Chem.* 34:140–151, 1991.
Williams, M. et al., "Emerging Molecular Approaches to Pain Therapy," *J. Med. Chem.* 42(9):1481–1500, May 1999.

\* cited by examiner

*Primary Examiner*—Taofiq Solola
(74) *Attorney, Agent, or Firm*—Seed IP Law Group PLLC

(57) ABSTRACT

The invention provides aminoalkylindole compounds of Formula (I), wherein $R_1$–$R_5$, n and p are as described. Also provided are compositions containing compounds of Formula (I) and the use of compounds of Formula (I) in modulating the activity of a cannabinoid receptor in a subject. In particular, the invention provides the use of such compounds as analgesic agents

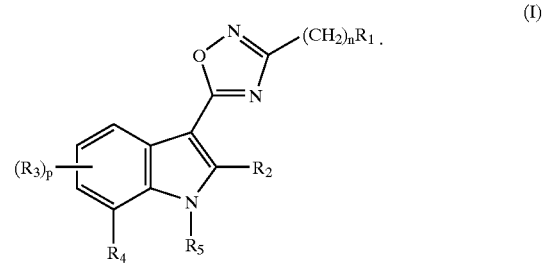

17 Claims, No Drawings

3-OXADIAZOL-5-YL-1-AMINOALKYL-1H-INDOLE DERIVATIVES

FIELD OF THE INVENTION

The present invention relates generally to compounds having affinity for cannabinoid receptors. In particular, the invention relates to indole derivatives having said affinity, compositions containing them and their use as modulators of cannabinoid receptor activity in therapy.

BACKGROUND TO THE INVENTION

Over the last decade or so, aminoalkylindoles (AAIs) have attracted considerable attention as ligands of the cannabinoid $CB_1$ and $CB_2$ receptors. Various members of this group of compounds have been identified as either nonselective ligands, $CB_1$ agonists, $CB_2$ agonists, or as antagonists of these receptors (1–8). Various AAIs have also been suggested as being useful tools in pharmacological studies of cannabinoid ligands and cannabinoid receptors. Compounds, including AAIs, with activity at cannabinoid receptors have been suggested as being of use in a wide variety of therapeutic applications including anti-inflammatory, anti-glaucoma and immunosuppressant applications. One indication of particular interest for treatment by compounds with cannabinoid activity is pain therapy (5).

A typical example of the AAIs previously described is the generic structure provided as Formula I in U.S. Pat. No. 4,973,587

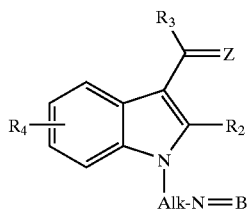

where: C(=Z)-$R_3$ is an arylcarbonyl group and Alk-N=B is a lower alkylene chain terminally substituted by a N,N-di-lower-alkylamino group, a 4-morpholinyl group, a 1-pyrrolidinyl or a 1-piperidinyl group.

Various structural modifications to this general structure have been explored, and one widely studied compound is designated as WIN-55212-2. WIN-55212-2 is structurally related to the other AAIs and includes an additional ring formed between the 7-position on the indole and C-1 of the alkyl chain at the 1-position on the indole core.

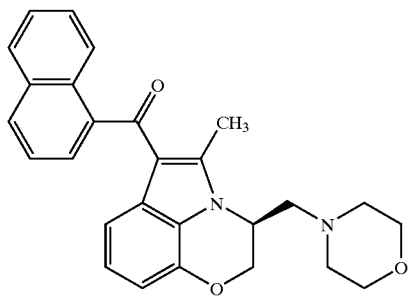

WIN-55212-2

A common structural feature of all of these previously reported AAIs is a carbonyl or thiocarbonyl group, further substituted by an aryl group, attached at the 3- or 4-position of the indole nucleus. Studies by Dutta et al. (1) pointed to the importance of the role of the keto group in the interaction of a number of AAIs with the cannabinoid receptor.

The present inventors have now surprisingly found that, in contrast to the findings by Dutta et al., the removal of the carbonyl group at C-3 of the indole nucleus and replacement thereof with a five membered heterocyclic group provides novel compounds which may exhibit useful activity at cannabinoid receptors.

SUMMARY OF THE INVENTION

Throughout this specification and the claims which follow, unless the context requires otherwise, the word "comprise", and or variations such as "comprises" or "comprising", will be understood to imply the inclusion of a stated integer or step or group of integers or steps but not the exclusion of any other integer or step or group of integers or steps.

In a first aspect, the present invention provides a compound of Formula (I):

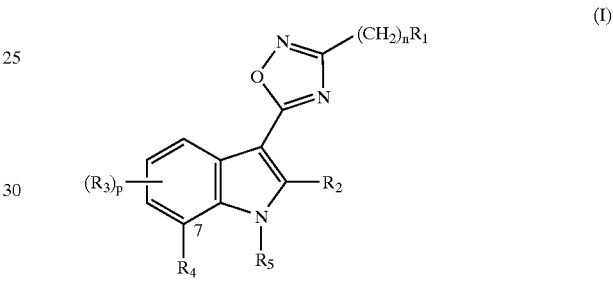

wherein
n is 0, 1 or 2;
$R_1$ is either:
a monocyclic group selected from the group consisting of 2-thienyl, 3-thienyl, 2-furanyl, 3-furanyl, 2-pyrrolyl, and 3-pyrrolyl, each of which may be unsubstituted or substituted 1 to 3 times by a substituent; styryl, or phenyl, each of which may be unsubstituted or substituted 1 to 4 times by a substituent; or phenyl or styryl, each substituted by methylenedioxy; or a polycyclic group selected from the group consisting of 1-naphthyl, 2-naphthyl, 2-biphenyl, 4-biphenyl, (1H-imidazol-1-yl)napththyl, 2-(1-naphthyl)ethenyl, 1-(1,2,3,4-tetrahydronaphthyl), anthryl, phenanthryl, pyrenyl, benzo[b]furyl, benzothienyl, indolyl, quinolyl, isoquinolyl and 1H-benzimidazolyl, each of which may be unsubstituted or substituted 1 to 4 times by a substituent;

wherein said substituents are independently selected from the group consisting of halogen, lower alkyl, lower alkoxy, hydroxy, nitro, cyano, amino, N-lower alkylamino, N,N-di-lower alkylamino, lower alkylthio, mercapto, lower alkylsulphinyl, lower alkylsulphonyl and trifluoromethyl;

$R_2$ is hydrogen, lower alkyl or halo;
p is 0, 1, 2 or 3;
each $R_3$ is independently selected from the group consisting of hydroxy, lower alkyl, lower alkoxy, halogen, mercapto, lower alkylthio, amino, N-lower alkylamino, N,N-di-lower alkylamino, nitro, trifluoromethyl and trifluoromethoxy;

when $R_5$ is $(CH_2)_m$-Het, $(CH_2)_m$—N=B or $(CH_2)_q$-Z, $R_4$ is selected from the group consisting of hydrogen, lower alkyl, lower alkoxy, halogen, mercapto, lower alkylthio, amino, N-lower alkylamino, N,N-di-lower alkylamino, nitro, trifluoromethyl and trifluoromethoxy; or when $R_5$ is $CHR_6CH_2$—N=B or $CHR_6CH_2$-Het, $R_4$ and $R_6$ together form a group —Y—$CH_2$— wherein Y is O or $CH_2$ and is bonded to the 7-position of the indole ring; or when $R_5$ is $CH_2CHR_8CH_2$—N=B or $CH_2CHR_8CH_2$-Het, $R_4$ and $R_8$ together form —O— or —$CH_2$—;

$R_5$ is selected from the group consisting of $(CH_2)_m$-Het, $(CH_2)_m$—N=B, $(CH_2)_q$-Z, $CHR_6CH_2$—N=B, $CHR_6CH_2$-Het, $CH_2CHR_8CH_2$—N=B and $CH_2CHR_8CH_2$-Het;

wherein m is 0, 1, 2, 3 or 4 and when m is not 0, a $CH_2$ group of the alkyl chain $(CH_2)_m$ may be substituted by lower alkyl; and q is 1, 2, 3 or 4, wherein a $CH_2$ group of the alkyl chain $(CH_2)_q$ may be substituted by lower alkyl;

Het is a heterocycle, attached at a carbon atom, selected from the group consisting of: 2-pyrrolidinyl, 3-pyrrolidinyl, 2-piperidinyl, 3-piperidinyl, 4-piperidinyl, 2-morpholinyl, 3-morpholinyl, 2-thiomorpholinyl or 5-oxide thereof, 3-thiomorpholinyl or 5-oxide thereof, 2-piperazinyl, tetrahydropuridinyl, azetidinyl, 2-, 3- or 4-hexahydroazepinyl, 2-, 3- or 4-hexahydro thiazepinyl, 2-indolinyl, 3-indolinyl, 1-isoindolinyl, 2-pyrrolyl, 3-pyrrolyl, 2-pyridinyl, 3-pyridinyl, 4-pyridinyl, 2-pyrazinyl, 2-pyrimidinyl and 4-pyrimidinyl;

wherein the carbon atoms of said heterocycle may be unsubstituted or 1, 2 or 3 carbon atoms may be independently substituted by oxo, hydroxy, lower alkyl or lower alkoxy; and the nitrogen atom of said heterocycle may be unsubstituted or substituted by lower alkyl, benzyl, lower alkylbenzyl, lower alkoxylbenzyl, halobenzyl, or benzhydryl;

—N=B is N,N-di-lower alkylamino, or a nitrogen attached heterocycle selected from the group consisting of 4-morpholinyl, 4-thiomorpholinyl, 4-piperazinyl, 1-pyrrolidinyl, or 1-piperidinyl wherein the carbon atoms of said heterocycle may be unsubstituted or 1, 2 or 3 carbon atoms may be independently substituted by hydroxy, lower alkyl or lower alkoxy;

Z is methyl, halogen or $CO_2R_7$ wherein $R_7$ is lower alkyl or hydrogen; and $R_4$ and $R_6$, and $R_4$ and $R_8$ together form a group as described above;

or a pharmaceutically acceptable salt or prodrug thereof.

In another aspect, the invention provides a composition comprising a compound of Formula (I) together with one or more additives. Preferred compositions are those comprising a compound of Formula (I) together with one or more pharmaceutically acceptable additives.

In yet a further aspect, the invention provides a method for modulating the activity of a cannabinoid receptor in a subject in need thereof comprising administering to said subject, a modulating effective amount of a compound of Formula (I).

Still another aspect of the invention relates to the use of a compound of Formula (I) in the preparation of a medicament for modulating the activity of a cannabinoid receptor.

Certain compounds of the invention may have particular utility as antinociceptive agents, ie., in the treatment or alleviation of pain, and thus may provide analgesic agents.

DETAILED DESCRIPTION OF THE INVENTION

As used herein, the term "lower alkyl", either used alone or in compound words such as lower alkoxy, lower alkylthio etc., refers to monovalent straight, branched or, where appropriate, cyclic aliphatic radicals having from 1 to 4 carbon atoms, ie., methyl, ethyl, n-propyl, iso-propyl, cyclopropyl, n-butyl, sec-butyl, t-butyl and cyclobutyl.

"Lower alkoxy" refers to a lower alkyl group bonded to an oxygen atom and "lower alkylthio" refers to a lower alkyl group bonded to a sulfur atom. Examples of lower alkoxy include methoxy, ethoxy, n-propoxy, iso-propoxy, cyclopropoxy, and butoxy (n-, sec-t- and cyclo). Examples of lower alkylthio include methylthio, ethylthio, n-propylthio and iso-propylthio.

Examples of N-lower alkylamino and N,N-di-lower alkyl amino include methylamino, ethylamino, n-propylamino, iso-propylamino, dimethylamino, diethylamino and di-isopropylamino.

The term "halogen" refers to fluorine, chlorine, bromine or iodine.

In certain preferred forms of the invention, the compounds of Formula (I) possess one or more of the following embodiments:

n is 1 or 2;

$R_1$ is phenyl, thienyl, 1-naphthyl, 2-naphthyl, or biphenyl, unsubstituted or substituted as described herein. Preferred substituents are hydroxy, lower alkyl eg. methyl or ethyl, lower alkoxy eg. methoxy, ethoxy n- or iso-propoxy, halogen eg. chlorine or bromine, amino, N-lower alkylamino eg. methylamino, ethylamino, N,N-di-lower alkylamino eg. dimethylamino, diethylamino, di-n- or iso-propylamino;

$R_2$ is hydrogen;

$R_3$ is hydroxy, methyl, ethyl, propyl, methoxy, ethoxy, propoxy, chloro, bromo, mercapto, methylthio, ethylthio, propylthio, amino methylamino, ethylamino, propylamino, dimethylamino, diethylamino, dipropylamino;

p is 0 or 1, more preferably 0;

$R_5$ is $(CH_2)_m$ Het or $(CH_2)_m$—N=B wherein m is preferably 1 or 2;

Het is preferably 2- or 3-morpholinyl, 2- or 3-thiomorpholinyl, 2-piperazinyl, 2- or 3-pyrrolidinyl, 2- or 3-piperidinyl each of which may be unsubstituted or substituted as described herein;

N=B is preferably 4-morpholinyl, 4-thiomorpholinyl, 1-piperazinyl, 1-pyrrolidinyl, 1-piperidinyl, unsubstituted or substituted as described herein, preferably by a substituent selected from the group consisting of hydroxy, methyl, ethyl, propyl, methoxy, ethoxy and propoxy.

In a preferred embodiment, each of $R_1$, Het or N=B is unsubstituted or substituted by one substituent.

A particularly preferred compound is 3-(3-benzyl-[1,2,4]-oxadiazol-5-yl)-1-[2-(pyrrolidin-1-yl)ethyl]-1H-indole (Compound 1).

The compounds of Formula (I) may be prepared using the general methods depicted in Scheme 1 as further described below. Unless otherwise stated $R_1$, $R_2$, $R_3$, $R_4$, $R_5$, p and n are as described above.

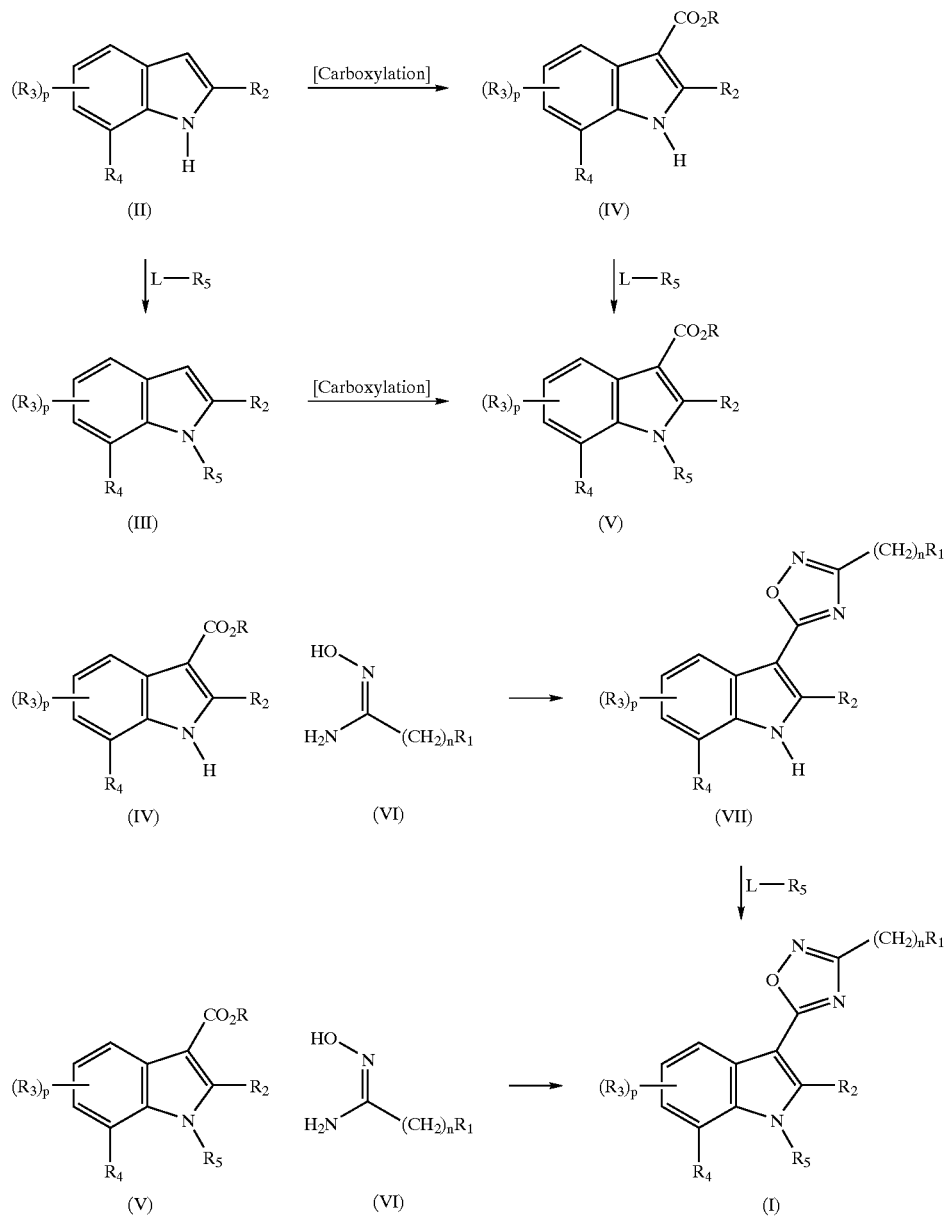

Scheme 1

In one embodiment, compounds of Formula (I) may be prepared by reacting an appropriately substituted indole-3-carboxylic acid or ester (IV) (eg where R is H or a lower alkyl group) with an appropriately substituted amidoxime (VI) for a time and under conditions suitable for the formation of oxadiazole (VII). Selection of appropriate conditions for the coupling reaction may be readily ascertained by those skilled in the art, and will typically involve a base, for example, carbonyldiimidazole or sodium hydride. N-Alkylation of the indole nitrogen of (VII) with a group of L-$R_5$ (where L is a leaving group) affords (I). Selection of suitable leaving groups are readily ascertained by those skilled in the art. Examples of suitable leaving groups include the halogens such as bromine, chlorine or iodine, and sulfonates such as mesylate, tosylate, brosylate, nosylate, or tresylate.

Alternatively, an indole-3-carboxylic acid or ester wherein the indole nitrogen is already substituted by the group $R_5$ (V) may be reacted with an appropriately substituted amidoxime (VI) for a time and under conditions suitable for the formation of oxadiazole (I).

Methods for N-alkylation are also readily determined by the skilled person, see for example Larock (10), page 397; Dutta et al. (1), Eissenstat et al. (2) and U.S. Pat. No. 4,973,587 (6), and may include reaction of the indole with L-$R_5$ (where L is a leaving group) in an inert solvent such as dimethylformamide, dimethyl sulfoxide, methanol, ethanol, or acetonitrile in the presence of a base such as NaH, $K_2CO_3$ or KOH.

Indole-3-carboxylic acids or esters (IV) and (V) may in some cases be commercially available, for example indole-3-carboxylic acid and methyl indole-3-carboxylate may be obtained from Aldrich, or may be prepared from indoles (II) and (III) by carboxylation using any of the methods known to those skilled in the art; for example (11–13), or may be prepared using any of methods known to those skilled in the art or reported in the chemical literature. In the indole-3-carboxylic acids or esters (IV) and (V), the group R is a hydrogen in the case of acids, or typically a lower-alkyl group in the case of esters. An indole (IV) may be converted to an indole (V) via N-alkylation of the indole nitrogen with a group L-R$_5$ wherein L is a suitable leaving group.

Indoles (II) and (III) may in some cases be commercially available, for example 2-methylindole, 4-methylindole, 5-methylindole, 6-methylindole, 7-methylindole, 4-methoxyindole, 5-methoxyindole, 6-methoxyindole, 7-methoxyindole, 4-chloroindole, 5-chloroindole, 6-chloroindole, 7-chloroindole, 4-nitroindole, 5-nitrooindole, 4-benzyloxyindole, 5-benzyloxyindole, 4-hydroxyindole, 5-hydroxyindole, 4-fluoroindole, 5-fluoroindole, 6-fluoroindole, 5-bromoindole, 7-bromoindole, 5,6-methylenedioxyindole, 5-methoxy-2-methylindole, 5-chloro-2-methylindole are available from Aldrich or Pfaltz & Bauer, or may be prepared using any of methods known to those skilled in the art or reported in the chemical literature. See for example the compounds and methods of preparation described for; Preparation 2A to 2-O, and 3A to 3D in U.S. Pat. No. 4,973,587 (6); Compounds of Formula II in U.S. Pat. No. 5,068,234 (7); Compounds of Formula IV in U.S. Pat. No. 4,939,138 (8); and indoles of formulae (5) and (6) in U.S. Pat. No. 6,013,648 (9).

Amidoximes (VI) may be prepared from the corresponding nitrile R$_1$(CH$_2$)$_n$CN by reaction with hydroxylamine for an appropriate time and under appropriate conditions. Those skilled in the art can readily determine suitable reaction times and conditions. Corresponding nitriles for the formation of amidoximes (VI) are in some cases commercially available or may be prepared from commercially available starting materials by any of the methods known to those skilled in the art.

Methods for the formation of compounds of Formula (I) wherein R$_4$ and R$_6$ or R$_4$ and R$_8$ together with the atoms to which they are attached form a cyclic group, are readily determined by the person skilled in the art, and may be carried out in accordance with the procedure described in U.S. Pat. No. 4,939,138 (8).

Those skilled in the art will realise that minor modifications to the methods described may be required to synthesise particular target compounds. General synthetic procedures applicable to the synthesis of the compounds may be found in standard references in the art of synthetic organic chemistry, for example Larock (10).

The term "salt, or prodrug" includes any pharmaceutically acceptable salt, ester, solvate, hydrate or any other compound which, upon administration to the recipient is capable of providing (directly or indirectly) a compound of Formula (I) as described herein. However, it will be appreciated that non-pharmaceutically acceptable salts also fall within the scope of the invention since these may be useful in non therapeutic applications and in the preparation of pharmaceutically acceptable salts. The term "pro-drug" is used in its broadest sense and encompasses those derivatives that are converted in vivo to the compounds of the invention. Such derivatives would readily occur to those skilled in the art, and include, for example, compounds where a free hydroxy group is converted into an ester, such as an acetate, or where a free amino group is converted into an amide. Procedures for acylating hydroxy or amino groups of the compounds of the invention are well known in the art and may include treatment of the compound with an appropriate carboxylic acid, anhydride or acylchloride in the presence of a suitable catalyst or base.

Esters of carboxylic acids are preferred and include esters formed from amino acids and alkyl acids. Preferred esters include C$_1$–C$_6$ alkyl esters wherein the alkyl group is a straight or branched chain, C$_5$–C$_7$ cycloalkyl esters, arylalkyl esters such as but not limited to benzyl, as well as amino acyl esters.

Suitable pharmaceutically acceptable salts include, but are not limited to, salts of pharmaceutically acceptable inorganic acids such as hydrochloric, sulphuric, phosphoric nitric, carbonic, boric, sulfamic, and hydrobromic acids, or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulphonic, toluenesulphonic, benezenesulphonic, salicyclic sulphanilic, aspartic, glutamic, edetic, stearic, palmitic, oleic, lauric, pantothenic, tannic, ascorbic and valeric acids. A preferred acid is tartaric acid so as to produce a tartrate salt.

Base salts include, but are not limited to, those formed with pharmaceutically acceptable cations, such as sodium, potassium, lithium, calcium, magnesium, ammonium and alkylammonium.

Basic nitrogen-containing groups may be quarternised with such agents as lower alkyl halide, such as methyl, ethyl, propyl, and butyl chlorides, bromides and iodides; dialkyl sulfates like dimethyl and diethyl sulfate; and others.

It will also be recognised that some compounds of formula (I) may possess asymmetric centres and are therefore capable of existing in more than one stereoisomeric form. The invention thus also relates to compounds in substantially pure isomeric form at one or more asymmetric centres eg., greater than about 90% ee, such as about 95% or 97% ee or greater than 99% ee, as well as mixtures, including racemic mixtures, thereof. Such isomers may be prepared by asymmetric synthesis, for example using chiral intermediates, or mixtures may be resolved by conventional methods, eg., chromatography, or use of a resolving agent.

Another aspect of the invention provides a method for modulating the activity of cannabinoid receptor comprising contacting said receptor with a modulating effective amount of a compound of Formula (I), or salt or prodrug thereof.

In particular, the invention provides a method for modulating the activity of a cannabinoid receptor in a subject in need thereof comprising administering to said subject, a modulating effective amount of a compound of Formula (I), or salt or prodrug thereof.

The invention also relates to the use of a compound of Formula (I), or salt or prodrug thereof, in the manufacture of a medicament for modulating the activity of a cannabinoid receptor and to agents therefor.

As used herein, the term "modulating" (or variations such as modulate or modulates) refers to regulation of the activity of a cannabinoid receptor. It will be understood that compounds which only partially up-regulate or down-regulate a cannabinoid receptor's activity may have useful therapeutic effects and thus, "modulating" also refers to partial up-regulation or partial down-regulation of receptor activity. Compounds of the present invention may therefore act as full or partial agonists, antagonists, or inverse agonists of a cannabinoid receptor.

The subject may be human or other animal such as a mammal. Non-human subjects include, but are not limited to primates, livestock animals (eg sheep, cows, horses, pigs, goats), domestic animals (eg dogs, cats), birds and laboratory test animals (eg mice, rats, guinea pigs, rabbits).

A long list of pharmacological properties, both in the CNS and in peripheral tissues, has been compiled for compounds active at cannabinoid receptors, including the analgesic, antiemetic, anti-inflammatory, bronchodilatory and anticonvulsant effects already known for cannabis preparations, but also the reduction of ocular pressure in glaucomic patients and the alleviation of neurological disorders such as multiple sclerosis, Huntington's chorea, spinal cord injury-associated spasticity and seizures (Eissenstat et al. (2) and Di Marzo et al. (26) and references therein). They have also been suggested as being useful as neuroprotective agents, appetite stimulants, antiparkinsonian agents, and for the treatment of asthma.

Compounds which act with selectivity as $CB_1$ agonists have been suggested as being useful in the treatment of a variety of conditions including pain, neuroprotection and lowering ocular pressure.

Compounds which act with selectivity as $CB_2$ agonists have been suggested (U.S. Pat. No. 6,013,648 (9) and Hanus et al. (27)) as being useful in the treatment of a variety of conditions including hypertension, inflammation, pain, autoimmune diseases, infectious diseases and allergic diseases. The following autoimmune diseases have been mentioned more particularly: systemic lupus erythematosus, connective tissue diseases, Sjogren's syndrome, ankylosing spondylarthritis, reactive arthritis, undifferentiated spondylarthritis, Behcet's disease and hemolytic autoimmune anemia. The allergic diseases to be treated can be of the immediate hypersensitivity or asthma type, for example. Likewise, compounds with $CB_2$ activity and their pharmaceutically acceptable salts can be used to treat vascularitis, parasitic infections, amyloidosis and diseases affecting the plasmacyte line.

Antagonists of cannabinoid receptors have been suggested as being therapeutically useful, for example in the treatment of dependence disorders.

Compounds of the invention may be used to treat disorders (diseases or conditions) wherein the activity or inactivity of a cannabinoid receptor is implicated, eg conditions listed above including but not limited to inflammatory conditions, glaucoma, immunological reactions and the treatment of pain.

In particular, one or more compounds of the invention may have full or partial agonist activity at the CB1 receptor and thus may be useful as an analgesic agent in the treatment of pain.

As used herein the term "pain" is not intended to be limited to any particular form of pain, and may be acute (eg headache, simple muscle strain), neuropathic in nature (eg chronic back pain, phantom limb pain, pain associated with arthritis, cancer-associated pain, bone injury pain), the result of trauma or injury (eg surgery) or associated with a disease or condition of the body (eg arthritis, cancer). In a preferred embodiment, the pain to be treated is neuropathic pain.

As used herein the term "treating" or "treatment" in respect of pain includes prophylaxis of pain in a patient having a tendency to develop such pain, and the amelioration or elimination of the developed pain once it has been established or alleviation of the characteristic symptoms of such pain.

Accordingly, in another embodiment the present invention provides a method for treating pain in a subject in need of said treatment, comprising administering to said subject, a treatment effective amount of a compound of Formula (I), or salt or prodrug thereof.

The invention also relates to the use of a compound of Formula (I), or salt or prodrug thereof, in the manufacture of a medicament for treating pain.

As used herein, the term "effective amount" relates to an amount of compound which, when administered according to a desired dosing regimen, provides the desired modulating or therapeutic activity. Dosing may occur at intervals of minutes, hours, days, weeks, months or years or continuously over any one of these periods. A modulating effective amount is an amount of the compound which, when administered according to a desired dosing regimen, is sufficient to at least partially up-regulate or down-regulate the activity of a cannabinoid receptor. A therapeutic or treatment effective amount is an amount of the compound which, when administered according to a desired dosing regimen, is sufficient to at least partially attain the desired therapeutic effect, or delay the onset of, or inhibit the progression of or halt or partially or fully reverse the onset or progression of a particular condition being treated.

Suitable dosages may lie within the range of about 0.1 ng per kg of body weight to 1 g per kg of body weight per dosage. The dosage is preferably in the range of 1 µg to 1 g per kg of body weight per dosage, such as is in the range of 1 mg to 1 g per kg of body weight per dosage. In one embodiment, the dosage is in the range of 1 mg to 500 mg per kg of body weight per dosage. In another embodiment, the dosage is in the range of 1 mg to 250 mg per kg of body weight per dosage. In yet another preferred embodiment, the dosage is in the range of 1 mg to 100 mg per kg of body weight per dosage, such as up to 50 mg per kg of body weight per dosage.

Suitable dosage amounts and dosing regimens can be determined by the attending physician or veterinarian and may depend on the desired level and type of modulating activity, the particular condition being treated, the severity of the condition as well as the general age, health and weight of the subject.

The active ingredient may be administered in a single dose or a series of doses. While it is possible for the active ingredient to be administered alone, it is preferable to present it as a composition, preferably as a pharmaceutical composition.

Accordingly, in another aspect, the present invention provides a composition comprising a compound of Formula (I), or salt or prodrug thereof, together with a pharmaceutically acceptable additive.

The formulation of such compositions is well known to those skilled in the art. The composition may contain pharmaceutically acceptable additives such as carriers, diluents or excipients. These include, where applicable, all conventional solvents, dispersion agents, fillers, solid carriers, coating agents, antifungal and antibacterial agents, dermal penetration agents, surfactants, isotonic and absorption agents and the like. It will be understood that the compositions of the invention may also include other supplementary physiologically active agents such as anti-glaucoma, immunosuppressant, anti-inflammatory or analgesic agents.

The carrier must be pharmaceutically acceptable in the sense of being compatible with the other ingredients of the composition and not injurious to the subject. Compositions include those suitable for oral, rectal, nasal, topical (including buccal and sublingual), vaginal or parenteral (including subcutaneous, intramuscular, intraspinal, intravenous and intradermal) administration. The compositions may conveniently be presented in unit dosage form and may be prepared by any methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Compositions of the present invention suitable for oral administration may be presented as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g inert diluent, preservative disintegrant (e.g. sodium starch glycolate, cross-linked polyvinyl pyrrolidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Compositions suitable for topical administration in the mouth include lozenges comprising the active ingredient in a flavoured base, usually sucrose and acacia or tragacanth gum; pastilles comprising the active ingredient in an inert basis such as gelatin and glycerin, or sucrose and acacia gum; and mouthwashes comprising the active ingredient in a suitable liquid carrier.

Compositions suitable for topical administration to the skin may comprise the compounds dissolved or suspended in any suitable carrier or base and may be in the form of lotions, gel, creams, pastes, ointments and the like. Suitable carriers include mineral oil, propylene glycol, polyoxyethylene, polyoxypropylene, emulsifying wax, sorbitan monostearate, polysorbate 60, cetyl esters wax, cetearyl alcohol, 2-octyldodecanol, benzyl alcohol and water. Transdermal devices, including patches, may also be used to administer the compounds of the invention.

Compositions for rectal administration may be presented as a suppository with a suitable carrier base comprising, for example, cocoa butter, gelatin, glycerin or polyethyene glycol.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solutions which may contain anti-oxidants, buffers, bactericides and solutes which render the composition isotonic with the blood of the intended recipient; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage compositions are those containing a daily dose or unit, daily sub-dose, as herein above described, or an appropriate fraction thereof, of the active ingredient.

It should be understood that in addition to the active ingredients particularly mentioned above, the compositions of this invention may include other agents conventional in the art having regard to the type of composition in question, for example, those suitable for oral administration may include such further agents as binders, sweeteners, thickeners, flavouring agents disintegrating agents, coating agents, preservatives, lubricants and/or time delay agents. Suitable sweeteners include sucrose, lactose, glucose, aspartame or saccharine. Suitable disintegrating agents include corn starch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

The compounds of the invention may also be presented for use in veterinary compositions. These may be prepared by any suitable means known in the art. Examples of such compositions include those adapted for:

(a) oral administration, external application (eg drenches including aqueous and non-aqueous solutions or suspensions), tablets, boluses, powders, granules, pellets for admixture with feedstuffs, pastes for application to the tongue;

(b) parenteral administration, eg subcutaneous, intramuscular or intravenous injection as a sterile solution or suspension (c) topical application eg creams, ointments, gels, lotions etc It will be recognised that other therapeutically active agents may be used in conjunction with a compound of Formula (I). These may be administered simultaneously, either as a combined form (ie as a single composition containing the active agents) or as discrete dosages. Alternatively, the other therapeutically active agents may be administered sequentially or separately with the compounds of the invention.

In a preferred form of this embodiment, a compound of Formula (I) or its salt or prodrug is administered in conjunction with an analgesic agent. Suitable analgesic agents include the opiates (eg morphine) and the $\alpha_2$ adrenoreceptor agonists (eg clonidine and deximetitomidine).

Thus, the invention also relates to a kit or a combination comprising a compound of Formula (I), or salt or prodrug thereof, and a further physiologically active agent, eg an analgesic, wherein the kit or combination is adapted for simultaneous, sequential or separate administration of the compound of Formula (I), or salt or prodrug thereof, and physiologically active agent. Also provided is a composition comprising a compound of Formula (I), or a salt or prodrug thereof together with a physiologically active agent.

By virtue of their affinity for cannabinoid receptors the compounds of the invention may be used as laboratory reagents. Typically for such use the compounds would be labelled in some way, preferably radiolabelled.

The compounds of the invention may also be useful in screens to identify molecules with affinity for cannabinoid receptors. Those skilled in the art are familiar with such screens, and could readily establish such screens using compounds of the present invention, preferably labelled in the same way, preferably radiolabelled.

Unless the context indicates otherwise, reference to any prior art in this specification is not, and should not be taken as, an acknowledgment or any form of suggestion that that prior art forms part of the common general knowledge in Australia.

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

The invention will now be described with reference to the following examples which are included for the purpose of illustration only and are not intended to limit the generality of the invention hereinbefore described.

EXPERIMENTAL

Synthesis of Compounds of Formula (I)

Example 1

Compounds of Formula (VI)

Method A

N-Hydroxy-2-(4-methoxy-phenyl)-acetamidine (VIa)

A mixture of (4-methoxyphenyl)acetonitrile (2.00 g, 14 mmol) and hydroxylamine hydrochloride (1.94 g, 28 mmol) in ethanol (25 mL) was treated with triethylamine (4.4 mL) and heated at reflux for 16 hours after which the solvent was evaporated under reduced pressure. Sodium carbonate solution (10%, 100 mL) was added and the solution extracted with ethyl acetate (150 mL). The organic extract was dried, filtered and evaporated under reduced pressure to give a green solid which was purified by recrystallization from ethyl acetate/hexane to give 1.43 g (57%) of (Via) as pale green prisms. mp 163–170° C. (lit.[14] 108–109°). MS m/z 181 (M+1)+

By the same general method of Method A but substituting an appropriate nitrile, the following compounds were prepared:

N-Hydroxy-2-phenyl-acetamidine (VIb), cream solid. mp 163–170° C. (lit.[15] 670), MS m/z 151 (M+1)+.

N-Hydroxybenzenecarboximidamide (VIc), MS m/z 137 (M+1)+.

N-Hydroxy[1,1'-biphenyl]-4-carboximidamide (VId), MS m/z 213 (M+1)+.

N-Hydroxy-2-naphthalen-2-yl-acetamidine (VIe), cream needles. mp 117–119° C.

N-Hydroxy-isonicotinamidine (VIf), white needles. m.p. 132–134° C. (lit.[16] 178–179°), MS m/z 138 (M+1)+.

N-Hydroxy-benzamidine (VIg), cream needles, mp 112–114° C. (lit.[17] 79–80°), MS m/z 137 (M+1)+.

N-Hydroxy-3-phenylpropanimidamide (VIh), white powder, MS m/z 213 (M+1)+.

N-Hydroxy-2-thien-2-yl-acetamidine (VIi)

Method B

Sodium metal (0.38 g, 17 mmol) was added in small pieces to methanol (12 mL), and once cool, treated with a solution of hydroxylamine hydrochloride (1.14 g, 16 mmol) in methanol (20 mL). The mixture was stirred at room temperature for 40 minutes and filtered. The filtrate was treated with thien-2-acetonitrile (1.74 mL, 16 mmol) and heated at gentle reflux for 48 hours after which the solvent was evaporated under reduced pressure. The residue was purified by flash chromatography eluting with $CHCl_3$/MeOH (19:1), to give 1.07 g (49%) of (VIi) as a cream solid. mp 77° C. (lit.[18] 80°).

By the same general method as Method B but substituting an appropriate nitrile, the following compounds were prepared:

2-(4-nitrophenyl)-N-hydroxyethanimidamide (VIj), green powder. mp 154–156° C. (lit.[19] no melting point given). Found (C, 49.18; H, 4.36; N, 19.94% $C_8H_9N_3O_3$ requires C, 49.23; H, 4.65; N, 21.53%).

2-(4-Bromophenyl)-N-hydroxyethanimidamide (VIk), pale yellow powder. mp 132–134° C. (lit.[19] no melting point given). Found (C, 43.19; H, 3.79; N, 9.23% $C_8H_9BrN_2O$ requires C, 41.95; H, 3.96; N, 12.23%).

2-(2-Chlorophenyl)-N-hydroxyethanimidamide (VIl), white powder. mp 112–114° C.

2-(2,4-Dichlorophenyl)-N-hydroxyethanimidamide (VIm), yellow powder. mp 112–114° C. (lit.[19] no melting point given).

2-(2-methoxyphenyl)-N-hydroxyethanimidamide (VIn), viscous yellow oil. MS m/z 181 (M+1)+.

2-(4-Chlorophenyl)-N-hydroxyethanimidamide (VIo), yellow powder. mp 112–114° C. (lit.[14] 103–104°).

N-Hydroxy-3-phenyl-propionamidine (VIp), viscous yellow oil. MS m/z 165 (M+1)+.

Example 2

Compounds of Formula (VII)

3-(3-Benzyl-[1,2,4]oxadiazol-5-yl)-1H-indole (VIIb)

Indole-3-carboxylic acid (820 mg, 5.1 mmol) and carbonyldiimidazole (CDI) (914 mg, 5.6 mmol) were stirred in DME (20 mL) for 16 hours. To a stirred solution of N-hydroxy-2-phenyl-acetamidine (VIb) (766 mg, 5.1 mmol) in DME (20 mL), was added crushed molecular sieves (3 Å, 900 mg). The mixture was stirred at room temperature or 30 minutes and sodium hydride (60%, 205 mg, 5.1 mmol) was added. After stirring at room temperature for an additional 30 minutes, the amidoxime/sieves/sodium hydride mixture was added in one portion to the acid/CDI mixture and the resulting mixture was heated at gentle reflux for 24 hours. The solvent was removed under reduced pressure and the residue partitioned between ethyl acetate (50 mL) and sodium bicarbonate solution (5%, 50 mL). The entire mixture was filtered through a sintered glass funnel and the phases separated. The aqueous portion was washed with ethyl acetate (2×20 mL), and the combined organic extracts were dried, filtered and evaporated under reduced pressure to yield an oily yellow solid. The residue was purified by recrystallization from ethyl acetate/hexane to give 720 mg (51%) of (VIIb) as white crystals, mp 198–199° C.; MS m/z 276; $^1$H NMR ($CDCl_3$) δ 4.16 (2H, s, $CH_2$), 7.21–7.48 (8H, m, ArH), 8.02 (1H, m, ArH), 8.28 (1H, m, ArH), 8.70 (1H, bs, NH). Anal. ($C_{17}H_{13}N_3O$) C, H, N.

By the same general method as Example 2 but using the appropriate amidoxime of Formula (VI) and the appropriate indole-3-carboxylic acid or ester of Formula (IV), the following compounds were prepared:

3-(3-Thien-2-yl-methyl-[1,2,4]oxadiazol-5-yl)-1H-indole (VIIi), black powder. MS m/z 282 (M+1)+. MR555/50 and MJS741/60.

3-[3-(4-Bromobenzyl)-[1,2,4]oxadiazol-5-yl]-1H-indole (VIIh), black solid. MS m/z 354/356 (M+1)+.

3-[3-(4-Methoxy-benzyl)-[1,2,4]oxadiazol-5-yl]-1H-indole (VIIa), grey solid. MS m/z 306 (M+1)+.

3-[3-(2-Chlorobenzyl)-[1,2,4]oxadiazol-5-yl]-1H-indole (VIIl), pale brown powder. MS m/z 310/312 (M+1)+.

3-[3-(2,4-Dichlorobenzyl)-[1,2,4]-oxadiazol-5-yl]-1H-indole (VIIm), pale brown powder. MS m/z 345/347 (M+1)+. MR555/59

3-(3-Phenethyl-[1,2,4]oxadiazol-5-yl)-1H-indole (VIIh), pale pink powder. MS m/z 290 (M+1)+.

3-(3-Phenyl-[1,2,4]-oxadiazol-5-yl)-1H-indole (VIIg), fine white crystals. mp 172–173$_f$C MS m/z 262 (M+1)+.

2-(3-Biphenyl-[1,2,4]-oxadiazole-5-yl)-1H-indole (VIId), White powder. m.p. 138–140° C.

Example 3

Compounds of Formula (I)

(Compound 1): 3-(3-Benzyl-[1,2,4]-oxadiazol-5-yl)-1-[2-(pyrrolidin-1-yl)ethyl]-1H-indole To a stirred solution of 3-(3-benzyl-[1,2,4]oxadiazol-5-yl)-1H-indole (VIIb) (120 mg, 0.43 mmol) in dry DMF (2 mL) was added sodium hydride (60%, 38 mg, 0.95 mmol). The mixture was stirred at room temperature for 30 minutes and 1-(2-chloroethyl)pyrrolidine hydrochloride (81 mg, 0.48 mmol) was added. The mixture was stirred at room temperature for 30 minutes and at 100° for 24 hours after which the solvent was evaporated under reduced pressure. Sodium carbonate solution (10%, 30 mL) was added and the solution was extracted with ethyl acetate (20 mL). The organic extract was dried, filtered and evaporated under reduced pressure to give a yellow residue which was purified by flash chromatography eluting with $CHCl_3$/MeOH (19:1), to give 116 mg (72%) of (1) as a viscous yellow oil. MS m/z 373 (M+1)+; $^1$H NMR (methanol-$d_4$) δ 1.64 (4H, m, 2×$CH_2$), 2.39 (4H, m, 2×$CH_2$), 2.71 (2H, t, J 6.9 Hz, $CH_2$), 4.01 (2H, s, $CH_2$), 4.14 (2H, t, J 6.9 Hz, $CH_2$), 7.10–7.38 (8H, m, ArH), 7.94 (1H, s, H2), 8.06 (1H, m, H4). $^{13}$C NMR (methanol-$d_3$) δ 22.81, 31.53, 45.21, 53.59, 54.68, 100.0, 110.1, 120.5, 121.8, 123.0, 125.1, 126.5, 128.2, 128.6, 132.4, 135.9, 136.4, 169.1, 173.3. Citrate salt hydrate+ ethanol, Anal. ($C_{23}H_{24}N_4O \cdot C_6H_8O_7 \cdot H_2O \cdot C_2H_6O$) C, H, N.

A Second Synthesis Provided Compound 1 as Described Below

Sodium hydride (80%, 74 mg, 2.5 mmol) was added in one portion to solution of the oxadiazole in dry DMF (4 ml) and stirred at room temperature for one hour. Pyrrolidine hydrochloride, previously dried at 50C for 6 hours, was added and the mixture heated at 100° C. for 24 hours. After allowing the reaction mixture to cool to room temperature, the solvent was removed in vacuo and the residue taken up in ethyl acetate (25 ml) and 10% sodium bicarbonate solution (25 ml). The layers were separated, the aqueous phase extracted with ethyl acetate (2×25 ml) and the combined organic phrases dried ($Na_2SO_4$), filtered and the solvent removed giving an orange/brown oil. The material was purified by flash chromatography (chloroform:methanol; 9:1) to give Compound 1 as a pale yellow oil that crystallised on standing (289.5 mg, 86%), m.p. 59–60°; $^1$H NMR (MeOH-$d_4$) δ 1.79–1.81 (4H, m, 2×$CH_2$), 2.59 (4H, m, 2×$CH_2$), 2.96 (2H, t, J 6.9 Hz, $CH_2$), 4.12 (2H, s, $CH_2$Ph), 4.43 (2H, t, J 6.9 Hz, $CH_2$), 7.29–7.39 (7H, m, ArH), 7.57 (1H, bd, J 7.8 Hz, H7), 8.14–8.16 (1H, m, H4), 8.20 (1H, s, H2); $^{13}$C NMR (MeOH-d4) δ 22.8, 31.5, 45.3, 53.7, 54.8, 100.1, 110.1, 120.5, 121.8, 123.0, 125.2, 126.5, 128.2, 128.5, 132.6, 135.9, 136.6, 169.1, 173.4; MS in/z 373 (M++1, 100%).

Preparation of Tartrate Salt of Compound 1

Compound 1 (46.6 mg, 0.125 mmol) and (+)-tartaric acid (18.8 mg, 0.125 mmol) were heated under reflux in ethanol (distilled, 95%) for 10 minutes then the solvent removed under reduced pressure to give a creamy coloured foam. The material was recrystallised from ethanol (95%) to give colourless needles (25.4 mg, 39%), m.p. 105–116° C. $^1$H NMR (MeOH-d4) δ 1.99 (4H, m 2×$CH_2$), 3.18 (4H, m, 2×$CH_2$), 3.53–3.58 (2H, m, $CH_2$), 4.13 (2H, s, $CH_2$Ph), 4.66–4.70 (2H, m, $CH_2$), 7.25–7.42 (7H, m, ArH), 7.65 (1H, bd, J 9 Hz, H7), 8.18 (1H, bd, J 7.5 Hz, H4), 8.26 (1H, s, H2).

By the same general method as Example 3 but substituting the appropriate compound of Formula (VII) and the appropriate alkylating group L-$R_5$, the following compounds were prepared:

(Compound 2) 3-(3-Benzyl-[1,2,4]-oxadiazol-5-yl)-1-[2-(morpholin-4-yl)ethyl]-1H-indole colourless solid. MS m/z 389 (M+1)+.

(Compound 3) 3-(3-Phenyl-[1,2,4]-oxadiazol-5-yl)-1-[2-(morpholin-4-yl)ethyl]-1H-indole yellow crystals, mp 144–146° C.

(Compound 4) 1-[2-(Morpholin-4-yl)ethyl]-3-(3-thien-2-ylmethyl-[1,2,4]oxadiazol-5-yl)-1H-indole), yellow gum. MS m/z 395 (M+1)+.

(Compound 5) 3-(3-Benzyl-[1,2,4]oxadiazol-5-yl)-1-[2-(piperidin-1-yl)ethyl]-1H-indole viscous yellow oil. MS m/z 387 (M+1)+.

(Compound 6) 3-[3-(4-Methoxy-benzyl)-[1,2,4] oxadiazol-5-yl]-1-[2-(morpholin-4-yl)ethyl]-1H-indole, pale yellow powder. MS m/z 419 (M+1)+.

(Compound 7) 3-[3-(4-Bromo-benzyl)-[1,2,4]oxadiazol-5-yl]-1-[2-(morpholin-4-yl)ethyl]-1H-indole, yellow residue. MS m/z 467 (M+1)+.

(Compound 8) 3-(3-Benzyl-[1,2,4]oxadiazol-5-yl)-1-pentyl-1H-indole, colourless needles. Found (C, 76.40; H, 6.70; N, 12.10% $C_{22}H_{23}N_3O$ requires C, 76.49; H, 6.71; N, 12.16%).

(Compound 9) 1-[2-(morpholin-4-yl)ethyl]-3-(3-phenethyl-[1,2,4]oxadiazol-5-yl)-1H-indole, MS m/z 403.5 (M+1)+. Found (C, 71.40; H, 7.21; N, 13.39% $C_{24}H_{26}N_4O_2$ requires C, 71.74; H, 7.22; N, 13.39%).

(Compound 10) 3-[3-(2-Chlorobenzyl)-[1,2,4]-oxadiazol-5-yl]-1-[2-(morpholin-4-yl)ethyl]-1H-indole, yellow residue. MS m/z 423 (M+1)+. Found (C, 65.30; H, 5.45; N, 13.21% $C_{23}H_{23}N_4O_2$ requires C, 65.32; H, 5.48; N, 13.25%), (Compound 11) 3-[3-(Biphenyl)-[1,2,4]oxadiazole-5-yl]-1-[2-(morpholin-4-yl)ethyl]-1H-indole, white crystals, m.p. 138–140° C. (softens at m.p. 133° C.). MS m/z 451 (M+1)+. hplc retention time 27.51 minutes (Isocratic run 50B:50D (B=$CH_3CN:H_2O$ (10%)/D 0.05% TFA:$H_2O$) over 30 minutes.

(Compound 12) 3-[3-(naphth-2-ylmethyl)-[1,2,4]-oxadiazol-5-yl]-1-[2-(pyrolidin-1-yl)ethyl]-1H-indole.

(Compound 13) 3-[3-(naphth-2-ylmethyl)-[1,2,4]-oxadiazol-5-yl]-1-[2-(morpholin-4-yl)ethyl]-1H-indole.

(Compound 14) Ethyl 5-([3-(naphth-2-ylmethyl)-[1,2,4]-oxadiazole-5-yl]-1H-indol-1-yl)pentanoate, off-white oil. MS m/z 454 (M+1)$^+$. hplc retention time=21.51 minutes (Linear run 50B/50D (B=90% $CH_3CN$:10% $H_2O$/D=0.05% $H_3PO_4$:$H_2O$) over 30 minutes.

(Compound 15) 5-([3-(Naphth-2-ylmethyl)-[1,2,4]-oxadiazole-5-yl]-1H-indol-1-yl)pentanoic acid, Grey gum. MS m/z 426 (M+1)$^+$.

(Compound 16) Ethyl 3-([3-(naphth-2-ylmethyl)-1,2,4-oxadiazol-5-yl]-1H-indol-1-yl)propanoate, clear gum. MS m/z 426 (M+1)$^+$.

General Procedure for Tartrate Salt Formation

The free base form of a compound in ethanol is mixed with one equivalent of tartaric acid and the mixture heated at reflux for 10 minutes. The mixture is then evaporated to dryness to yield the tartrate salt of the compound.

Pharmacological Studies

The affinity of compounds at cannabinoid receptors is routinely assessed using ligand binding assays known to those skilled in the art. Radioligand binding assays were conducted using rat cerebellum or rat spleen. The cerebellum of the rat is known to express predominantly, if not exclusively, the $CB_1$ receptor subtype (20,21). Thus, binding constants obtained from these studies are characterised by a single affinity value, as only one receptor type is labelled. This was found to be the case for all compounds tested and thus the derived values represent binding affinity constants for the $CB_1$ receptor. The rat spleen possesses both $CB_1$ and $CB_2$ subtypes of cannabinoid receptor, with the latter being the predominating subtype (22,23). Hence, single affinity estimates were associated only with those compounds that showed no selectivity between $CB_1$ and $CB_2$ receptors. In contrast, biphasic binding curves in the spleen characterised by two affinity constants represent the profile of compounds showing selectivity for one receptor subtype over another. In order to determine the order of selectivity, the high and low affinity values obtained for these compounds in the spleen binding assays were compared to the single affinity estimates obtained for the cerebellum ($CB_1$) assays. Compounds for which the high affinity binding constant from the spleen correlated with the binding affinity constant from the cerebellum were concluded to be $CB_1$-selective. In contrast, compounds for which the low affinity binding constant from the spleen correlated with the binding affinity constant from the cerebellum were concluded to be $CB_2$-selective, and the high affinity constant from the spleen experiments was then taken as the measure of affinity for the $CB_2$ receptor.

Functional activity of the compounds was assayed using the mouse electrically-stimulated vas deferens bioassay, a measure of $CB_1$ receptor function (24,25). Compounds showing appreciable activity in this assay and the ability to be antagonised by the $CB_1$-selective antagonist, SR141716A, were deemed to be $CB_1$ agonists. The remaining compounds were classed as cannabinoid ligands. $CB_2$ functionality may be investigated using assays known to those skilled in the art; for example those described in U.S. Pat. No. 6,013,648.

Example 4

Radioligand Binding Assays

Rat Cerebellum

Sprague Dawley rats of either sex (200–300 g) were killed by gassing with 80% $CO_2$ in $O_2$ and decapitation, and the entire brain excised rapidly and placed in ice-cold Tris-HCl buffer (Tris 50 mM, $MgCl_2$ 3 mM, EGTA 0.2 mM, pH to 7.4 with HCl). On ice, the cerebellum was dissected away from the rest of the brain, weighed and homogenised (PT-DA 1205/2EC Polytron Aggregate; Kinematica, Luzernerstrasse Switzland) in 10 volumes of ice-cold Tris-HCl buffer. The homogenate was then made up to 20 volumes and centrifuged (Model J2-M1, Beckman, Fullerton, Calif., U.S.A.) at 31,000 for 15 min at 4° C.). Subsequently, the supernatant was discarded, the pellet resuspended in 20 volumes of buffer and centrifuged as before. The resulting pellet was then resuspended in 20 volumes of buffer and assayed for protein content using the method of Bradford (Bradford, 1976) in a Novaspec II spectrophotometer (Pharmacia Biotech; with bovine serum albumin (BSA; Homosafe BSA, c/o 'ScimaR' Templestowe, Australia) as the standard. The homogenate was then recentrifuged and the final pellet resuspended in Tris-HCl buffer at a protein concentration of 5 mg/ml and stored in 500 µl aliquots at −80° C. until used in the binding assay.

Rat Spleen

Sprague Dawley rats (200–300 g) were killed by gassing with 80% $CO_2$ in $O_2$ and decapitation and the spleen excised rapidly and placed in ice-cold Tris-HCl buffer (Tris 50 mM, $MgCl_2$ 3 mM, EGTA 0.2 mM, pH 7.4). The spleen was weighed and diced using a scalpel before homogenisation in 10 volumes of Tris-HCl buffer. The homogenate was then made up to 20 volumes and centrifuged (12,600 g, 5 min, 4° C.), the supernatant was retained and centrifuged (23,800 g, 20 min, 4° C.). The pellet was resuspended in 10 volumes of buffer and assayed for protein content using the method of Bradford (Bradford, 1976) with BSA as the standard. The homogenate was then recentrifuged and the final pellet resuspended in Tris-HCl buffer at a protein concentration of 5 mg/ml and stored in 500 µl aliquots at −80° C. until used for the binding assay.

Radioligand Binding Protocol

Ligand binding assays were performed in polypropylene tubes in a total volume of 1 ml containing Tris-HCl buffer, a final concentration of 1 mg/ml BSA, and varying concentrations of drugs. Tubes contained 30 µg of membrane protein and incubation was started by the addition of 100 µl of either 0.5 nM [$^3$H]SR141716A or 0.2 nM [$^3$H]WIN 55,212-2. Experiments were carried out in triplicate at 30° C. for 90 min with non-specific binding being defined as radioligand binding in the presence of 1 µM unlabelled WIN 55,212-2. Incubations were terminated by rapid filtration with a M-24 Cell Harvester (Brandel; Gaithersburg, Md., U.S.A.) using ice-cold Tris-HCl buffer containing 0.5 mg/ml BSA. Filters (Wattman GF/B) were soaked for 2 h prior to filtering in a solution of Tris-HCl buffer containing 3 mg/ml BSA and 0.5% w/w polyethyleneimine (PEI). Filters were left to dry thoroughly before placement into scintillation vials with 5 ml of scintillation cocktail (Ultima Gold LSC-cocktail; Packard Bioscience, Meriden, Conn., U.S.A.) being added. Vials were left to stand overnight before the radioactivity was determined using a Model 1409 DSA Liquid Scintillation counter (EG&E Wallac, Gaithersburg, Md., U.S.A.).

Data Analysis

The resulting radioligand binding curves were analyzed by nonlinear regression using the program PRISM 3.0 (GraphPad Software, San Diego, Calif.) in order to derive ligand affinity estimates for the cannabinoid receptor(s).

Drugs and Chemicals

[$^3$H]SR141716A (Amersham Pharmacia Biotech Piscataway, N.J., U.S.A.), [$^3$H]WIN55,212-2 (Du Pont), Bio-Rad protein assay dye reagent concentrate (Bio-Rad, Hercules, Calif., U.S.A.), ethyleneglycol-bis(β-aminoethyl ether)-N,N,N',N'-tetraacetic acid (EGTA; Sigma Chemical Co., St Louis, Mo., U.S.A.), Tris Ultrapure (ICN Biomedicals Inc, Ohio, U.S.A). All other reagents were obtained from Sigma Chemical Co.

Example 5

Mouse Isolated Vasa Deferenitia

Swiss white mice (35–40 g) were killed by exposure to 80% $CO_2$ in $O_2$ and exsanguination. Mouse vasa deferentia were dissected with capsular connective tissue intact and set up in 20 ml organ baths at 37° C. in $Mg^{2+}$-free physiological salt solution. The upper (epididymal) end was attached to an isometric force transducer (Grass FTO3C) and the lower (prostatic) end tied to a fixed support between two parallel platinum field electrodes (5 mm apart, 5 mm long). The tissue was initially stretched by 0.5 g force and allowed to equilibrate 10 min. The tissues were stimulated (Grass S88 stimulator) to contract using trains of electrical field stimulation of 3 pulses (4 Hz), 0.5 ms duration, 100 V (80% maximal voltage) every 20 s for 10 min. This electrical stimulation period was applied before and after both antagonist and agonist addition. Output from the transducer amplifier was recorded on a flat bed recorder (Gould BS 272, Cleveland, Ohio, U.S.A.). All drugs were dissolved in dimethyl sulfoxide (DMSO; Sigma, St Louis, Mo., U.S.A.) and allowed to equilibrate with the tissue for 30 min before the responses to field stimulation were assessed. Drug effects were measured as the percentage decrease of the pre-drug twitch force. In experiments where only a single drug concentration was tested, the resulting effect was expressed as a percentage of that observed in the presence of vehicle. Binding data and data in the mouse vas deferens assay for some compounds are summarised in Table 1.

TABLE 1

| Compound Number | $CB_1$ (MVD) % inh at 1.0 μM | $CB_1$ (Binding) $IC_{50}$ (μM) | $CB_2$ (Binding) $IC_{50}$ (μM) |
| --- | --- | --- | --- |
| Anandamide | 84 | 1 | <1 |
| THC | 100 | 0.1 | <0.1 |
| WIN-55212 | 100 | — | — |
| (1) as tartrate | 80 | 0.05 | 1.6 |
| (2) | 96 | 1 | 1 |
| (3) | 83 | 1 | 1 |
| (4) | 81 | 0.1 | — |
| (5) | 46 | — | — |
| (6) | 39 | 0.2 | 2.8 |
| (7) | 58 | — | — |
| (8) | 100 | 0.006 | 0.4 |
| (9) | 90 | — | 1.2 |
| (10) | 95 | — | — |
| (11) | 11 | >>10 | >>10 |
| (12) | 96 | — | — |
| (13) | 54 | — | — |
| (14) | 42 | — | — |
| (15) | 54 | — | — |
| (16) | 77 | — | — |

— means assay not performed

Example 6

Antinociceptive Testing

Intrathecal Administration

The following sequence protocol was used for the acute intrathecal administration to Sprague-Dawley rats. Each rat only underwent one cycle of the sequence protocol:

| | |
| --- | --- |
| Day −1 | Pre-surgery antinociception testing |
| Day 0 | Intrathecal catheter placement (surgery) |
| Day 4 | Pre-treatment antinociception testing |
| | TREATMENT |
| | 10 μl volume of active drug/vehicle |
| | flushed with 10 μl 0.9% saline |
| | Post-treatment antinociception testing 15 min |
| | 30 min |
| | 60 min |
| | 120 min |
| Day 5 | Post-treatment antinociception testing 24 h |
| Day 6 | Administer Evan's Blue (to observe diffusion of dye intrathecally) |
| | Administer lignocaine 2% (to confirm catheter placement in L5/L6 spinal cord level by temporary paralysis of hind limbs) |
| | Fix rat with formalin (see section 2.2.3) |
| | Dissect out spinal cord and note any macroscopic changes |
| | Stain segments histologically to check for myelin and Nissyl cell damage |

Intrathecal Catheter Placement

Catheter Design

The catheters were made from PE-10 polyethylene tubing (non radiopaque) with an internal diameter of 0.28 mm and external diameter of 0.61 mm (Clay Adams, N.J., U.S.A.). A loose knot was established two-thirds along the length of a ~16 cm tubing and covered with dental acrylic (cold curing). Prior to surgery the longer end of the catheter was stretched and subsequently cut down to 8.5 cm in length, soaked in alcohol and flushed with saline.

Surgery

Intrathecal catheter placement was carried out as first described by Yaksh and Rudy (1976) The general thrust of the catheter placement involves the PE-10 catheter inserted into the subarachnoid space via the antlanto-occipital membrane (as the entry point) and threaded down to the lumber expansion of the spinal cord (spinal cord level L5/L6). The catheter tip is then exteriorised over the forehead. All animals are, assessed for normal motor function and behaviour post-surgery.

The following is an outline of the intrathecal catheter operating procedure:

Animal

Male Sprague Dawley rat 200–220 g

Anaesthesia

Standard halothane technique

Preparation

Intraperitoneal injection (5 ml) of saline, and shaving of dorsal side of neck. Rat is then placed in a stereotactic frame and kept in place using holder-pins inserted into the external auditory canal, and checked for symmetry and free antero-posterior movement of head but no lateral movement. Eye ointment is applied and skin is prepped with alcohol and betadine swab.

Operation

An incision is made along the dorsal midline of the head, the occiput groove identified and nuchal skin is incised and retracted caudally. The dorsal neck muscle tendinous insertion into the occipital ridge is cut bilaterally, then the occiput and antlanto-occipital membrane scraped with a rongeur. Spinal muscles are held back using an anchored dorsal hooked retractor. Following this, the dura is incised longitudinally for ~0.5 mm carefully, to avoid stabbing the cervical cord/medulla. At this point, cerebro-spinal fluid should flow out of the incision. Gently insert catheter into the subarachnoid space, keeping it low against the occiput, and advance slowly, while observing any twitches of flank or leg muscles or changes in respiration. Tail traction may aid at this point. The catheter is advanced 8.5 cm with the knot tucked immediately behind the nuchal crest. A needle is then inserted from the scalp midline (anterior to the ears), the catheter tip passed through it, and needle retracted back so catheter tip lies midline between the eyes. Incision is sutured and catheter flushed with saline to check for 'popcorning' (involuntary movements of the hind limbs) which indicates intra-cord placement.

Intravenous Administration

The following is the protocol adopted for all i.v. administration experiments in conscious Sprague-Dawley rats.

| Day −1 | Pre-surgery nociception testing |
| Day 0 | Jugular vein and femoral artery catheterisation. |
| Day 1 & 2/ 1 & 3 | Rat set up. |

Rats were used in two separate experiments with 24–48 h between each experiment. On the day of the experiment, rats were allowed to acclimatise in clear perspex chambers for 10 min. After this, the femoral artery catheter was bled (1 drop) to remove the clot and connected to a pressure transducer (CDX, Cobe, Lakewood, Colo., U.S.A.) for the measurement of phasic and mean arterial pressure (MAP). The blood pressure signal triggered a rate meter (Model 173; Baker Medical Research Institute, Prahran, Victoria, Australia) for the measurement of heart rate (HR). The jugular vein catheter was for administration of drugs. Phasic blood pressure, mean arterial pressure and heart rate were continuously recorded throughout the experiment on a Grass polygraph (Model 7D; Grass Instrument Co., Quincy, Mass., U.S.A.). The rats rested quietly in their separate compartments for 30 min prior to commencement of the experiment.

Drugs were administered in a 0.1 ml volume followed by 0.1 ml saline (0.9% sodium chloride solution; Baxter, Toongabbie, N.S.W., Australia) flush. Tail flick nociception was measured at 15, 30, and in the case of 0.1 mg/kg CP 55,940, 45 min after intravenous administration.

At the end of the experimental day, rats were either returned to the animal house or euthanased with an overdose of pentobarbitone sodium (~160 mg/kg, Lethabarb) given i.v. via the jugular vein catheter.

Antinociception Testing

The antinociception tests were all conducted using the Plantar Test Instrument (Ugo Basile, Varese, Italy) which comprises a movable infra-red (IR) heat source, a glass pane onto which the 3-compartment rat enclosure is placed and a controller. The IR heat source resides under the glass floor and is focussed onto the underside of the tail or hindpaw of an unrestrained rat. The test is commenced as soon as the IR heat source is activated and a digital timer determines the withdrawal latency to the nearest 0.1 s. The withdrawal latency is measured by the time difference between the activation of the IR heat source and physical withdrawal of the paw or tail from the stimulus.

Plantar Test

This test was used to assess the thermal withdrawal latency of the plantar part of the hindpaw to a focussed heat stimulus in order to examine thermal analgesia/hyperalgesia. After acclimation, a total of one warm-up and three real readings of withdrawal latency are taken for each hindpaw of every rat at IR 40 or IR 80 intensity, with two min between each reading to allow the hindpaw to return to baseline temperature. The average of the three readings is used in analysis.

Tail Flick Test

This test was used to assess the withdrawal latency for the tail to flick in response to a focussed heat source to determine the presence of analgesia/hyperalgesia. After acclimation, one warm-up and three actual measurements are conducted at IR 80 intensity, allowing two min between measurements to ensure the cooling down of the tail to basal body temperature. Rats who exhibit a tail flick withdrawal latency over 5.0 s during the pre-treatment measurements are discarded from the study.

A total of three measurements was chosen because statistical analysis comparing the standard error of the mean generated from three versus five readings showed very little difference. Three readings are also sufficient to observe any outliers in latency response while discouraging any conditioning of the rat to the stimulus.

Data Analysis

Drug effects were measured as absolute tail flick time (s) and as a % of Maximum Possible Effect (% MPE) by the following equation: % MPE=[(Test latency−Control latency)/(Cut-off time−Control latency)]×100. The peak drug effect data were fitted to a logistic curve using nonlinear regression (Kaleidagraph). From these logistic curve fits $pED_{50}$ values (the -log dose of drug required to cause 50% of the maximal possible antinociceptive effect) were compared using 1-way ANOVA with a Tukey-Kramer post-hoc test for multiple comparisons if appropriate.

Compound (1) tested as its tartrate salt provided an antinociceptive effect when given by either the i.t or the i.v route.

Neuropathic Pain Testing

Production of a unilateral hind limb neuropathy in male Sprague-Dawley rats was achieved using the technique of L5 and L6 spinal nerve ligation, according to the method of Kim and Chung (1992). Animals were given one week to recover from surgery prior to testing for the development of naturopathic pain.

The testing procedure involved the determination of tactile allodynia using von Frey hairs, which were applied sequentially to the plantar surface of the rat paw starting with 2 g of force and proceeding upwards to a maximum of 15.1 g of force or downwards to a minimum of 0.4 g force. The 15.1 g force was used to define the maximum possible effect (MPE) for this test of neuropathic pain. Once paw withdrawal occurred, the 50% withdrawal threshold was determined using the "up-down" method as published by Dixon (1980). Both hind paws were tested. Response to therapy as measured by tactile allodynia threshold was calculated using the percentage maximum possible effect (% MPE) according to the following equation: % MPE=100× ([Measured value]−[Pre-treatment value])/([MPE]−[Pre-treatment value]).

Drugs were dissolved in a propylene glycol vehicle and administered via intraperitoneal injection. Compound (1) tested as its tartrate salt caused a significant antinociceptive effect in this model of neuropathic pain.

REFERENCES

1. Dutta T. E., et al., *Bioorg. Med. Chem.*, 5, 1591–1600 (1997).
2. Eissenstat M. A., et al. *J. Med. Chem.*, 38, 3094–3105 (1995)
3. D'Ambra T. E., et al., *J. Med. Chem.*, 35, 124–135 (1992)
4. D'Ambra T. E., et al, *Bioorg. Med. Chem. Lett.*, 6, 17–22 (1996)

5. Williams M., et al. *J. Med. Chem.*, 42, 1481–1500 (1999)
6. U.S. Pat. No. 4,973,587
7. U.S. Pat. No. 5,068,234
8. U.S. Pat. No. 4,939,138
9. U.S. Pat. No. 6,013,648
10. Larock, R. C, *Comprehensive Organic Transformations—A guide to functional group preparations*, VCH Publishers, 1989.
11. Kelarev. V. I. et al.; *Zh. Org. Khim* 1992, 28, 2561–2568
12. Melzer, M. S.; *J. Org. Chem.* 1962, 27,496.
13. Doyle, F. P. et al.; *J. Chem. Soc.* 1959, 2853.
14. Bell, C. L., et al., *J. Org. Chem.*, 1964, 29(10), 2873–2877
15. Knudsen, P., *Chemishe Berichte*, 1885, 18, 1068–1074.
16. Bernasek, E. *Bull. Soc. Chem. Biol.* 1956, 38, 231–242
17. Tiemann, F. et al., *Ber.*, 1884, 17, 1685–1698
18. Bercot-Vatteroni, M. et al., *Ann. Chim.* 1962, 7, 303–337
19. Shea, P. J., Patent Belg. 826, 325 (C1.A61K), 05 Sep. 1975
20. Matsuda L. A., et al., *Nature*, 346(6284); 561–564 (1990)
21. Griffin G., et al., *Eur. J. Pharmacol.*, 377(1): 117–125 (1999)
22. Lynn A. B., et al., *J. Pharmacol. Exp. Ther.*, 268(2): 644–650 (1998)
23. Rinaldi-Caromna M., et al. *J. Pharmacol. Exp. Ther.*, 284(2): 644–650 (1998)
24. Pertwee R. G., et al., *Br. J. Pharmac*, 105(104): 980–984 (1992).
25. Lay L., et al., *Eur. J. Pharmacol.*, 391(1–2): 151–161 (2000)
26. Di Marzo V. et al., *Internet Journal of Science—Biological Chemistry*, "The endogenous cannabinoid signalling system: chemistry, biochemistry and physiology" (1997)
27. Hanus L. et al., *Proc. Nat. Acad. Sci.*, 96, 14228–14233 (1999)
28. Dixon, W. J., *Ann. Rev. Pharmacol. Toxicol.*, 20: 441–462 (1980)
29. Kim, S. and Chung, J., *Pain*, 50: 355–363 (1992)
30. Bradford, M. M., *Anal. Biochem.*, 72, 248–254 (1976)
31. Yaksh, T. L., and Rudy, T. A., *Physiol. and Behav.*, 17, 1031–1036 (1976)

What is claimed is:

1. A compound of Formula (I):

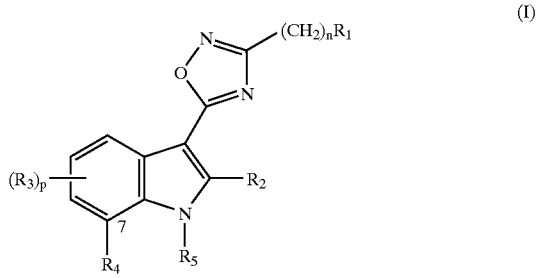

wherein n is 0, 1 or 2;

$R_1$ is either:

a monocyclic group selected from the group consisting of 2-thienyl, 3-thienyl, 2-furanyl, 3-furanyl, 2-pyrrolyl, and 3-pyrrolyl, each of which may be unsubstituted or substituted 1 to 3 times by a substituent; styryl, or phenyl, each of which may be unsubstituted or substituted 1 to 4 times by a substituent; or phenyl or styryl, each substituted by methylenedioxy; or a polycyclic group selected from the group consisting of 1-naphthyl, 2-naphthyl, 2-biphenyl, 4-biphenyl, (1H-imidazol-1-yl)napththyl, 2-(1-naphthyl)ethenyl, 1-(1,2,3,4-tetrahydronaphthyl), anthryl, phenanthryl, pyrenyl, benzo[b]furyl, benzothienyl, indolyl, quinolyl, isoquinolyl, and 1H-benzimidazolyl, each of which may be unsubstituted or substituted 1 to 4 times by a substituent;

wherein said substituents are independently selected from the group consisting of halogen, lower alkyl, lower alkoxy, hydroxy, nitro, cyano, amino, N-lower alkylamino, N,N-di-lower alkylamino, lower alkylthio, mercapto, lower alkylsulphinyl, lower alkylsulphonyl, and trifluoromethyl;

$R_2$ is hydrogen, lower alkyl or halo;

p is 0, 1, 2 or 3;

each $R_3$ is independently selected from the group consisting of hydroxy, lower alkyl, lower alkoxy, halogen, mercapto, lower alkylthio, amino, N-lower alkylamino, N,N-di-lower alkylamino, nitro, trifluoromethyl and trifluoromethoxy;

when $R_5$ is $(CH_2)_m$-Het, $(CH_2)_m$—N=B or $(CH_2)_q$-Z, $R_4$ is selected from the group consisting of hydrogen, lower alkyl, lower alkoxy, halogen, mercapto, lower alkylthio, amino, N-lower alkylamino, N,N-di-lower alkylamino, nitro, trifluoromethyl and trifluoromethoxy; or when $R_5$ is $CHR_6CH_2$—N=B or $CHR_6CH_2$-Het, $R_4$ and $R_6$ together form a group —Y—$CH_2$— wherein Y is O or $CH_2$ and is bonded to the 7-position of the indole ring; or when $R_5$ is $CH_2CHR_8CH_2$—N=B or $CH_2CHR_8CH_2$-Het, $R_4$ and $R_8$ together form —O— or —$CH_2$—;

$R_5$ is selected from the group consisting of $(CH_2)_m$-Het, $(CH_2)_m$—N=B, $(CH_2)_q$-Z, $CHR_6CH_2$—N=B, $CHR_6CH_2$-Het, $CH_2CHR_8CH_2$—N=B and $CH_2CHR_8CH_2$-Het;

wherein m is 0, 1, 2, 3 or 4 and when m is not 0, a $CH_2$ group of the alkyl chain $(CH_2)_m$ may be substituted by lower alkyl; and q is 1, 2, 3 or 4, wherein a $CH_2$ group of the alkyl chain $(CH_2)_q$ may be substituted by lower alkyl;

Het is a heterocycle, attached at a carbon atom, selected from the group consisting of: 2-pyrrolidinyl, 3-pyrrolidinyl, 2-piperidinyl, 3-piperidinyl, 4-piperidinyl, 2-morpholinyl, 3-morpholinyl, 2-thiomorpholinyl or 5-oxide thereof, 3-thiomorpholinyl or 5-oxide thereof, 2-piperazinyl, tetrahydropuridinyl, azetidinyl, 2-, 3- or 4-hexahydroazepinyl, 2-, 3- or 4-hexahydro thiazepinyl, 2-indolinyl, 3-indolinyl, 1-isoindolinyl, 2-pyrrolyl, 3-pyrrolyl, 2-pyridinyl, 3-pyridinyl, 4-pyridinyl, 2-pyrazinyl, 2-pyrimidinyl and 4-pyrimidinyl;

wherein the carbon atoms of said heterocycle may be unsubstituted or 1, 2 or 3 carbon atoms may be independently substituted by oxo, hydroxy, lower alkyl or lower alkoxy; and the nitrogen atom of said heterocycle may be unsubstituted or substituted by lower alkyl, benzyl, lower alkylbenzyl, lower alkoxylbenzyl, halobenzyl, or benzhydryl;

—N=B is N,N-di-lower alkylamino, or a heterocycle selected from the group consisting of 4-morpholinyl, 4-thiomorpholinyl, 4-piperazinyl, 1-pyrrolidinyl, or 1-piperidinyl wherein the carbon atoms of said heterocycle may be unsubstituted or 1, 2 or 3 carbon atoms may be independently substituted by hydroxy, lower alkyl or lower alkoxy; and Z is halogen or $CO_2R_7$ wherein $R_7$ is lower alkyl or hydrogen;

or a pharmaceutically acceptable salt or prodrug thereof.

2. A compound according to claim 1, or pharmaceutically acceptable salt or prodrug thereof, wherein n is 1 or 2.

3. A compound according to claim 1, or pharmaceutically acceptable salt or prodrug thereof, wherein $R_1$ is phenyl, thienyl, 1-napthyl or biphenyl, each of which may be unsubstituted or substituted.

4. A compound according to claim 1, or pharmaceutically acceptable salt or prodrug thereof, wherein $R_2$ is hydrogen.

5. A compound according to claim 1, or pharmaceutically acceptable salt or prodrug thereof, wherein p is 0 or 1.

6. A compound according to claim 1, or pharmaceutically acceptable salt or prodrug thereof, wherein $R_3$ is selected from the group consisting of hydroxy, methyl, ethyl, propyl, methoxy, ethoxy, propoxy, chloro, bromo, mercapto, methylthio, ethylthio, propylthio, amino, methylamino, ethylamino, propylamino, dimethylamino, diethylamino and dipropylamino.

7. A compound according to claim 1, or pharmaceutically acceptable salt or prodrug thereof, wherein $R_5$ is $(CH_2)_m$-Het, wherein Het is 2- or 3-morpholinyl, 2- or 3-thiomorpholinyl, 2-piperazinyl, 2- or 3-pyrrolidinyl, 2- or 3-piperidinyl, each of which may be substituted or unsubstituted.

8. A compound according to claim 1, or pharmaceutically acceptable salt or prodrug thereof, wherein $R_5$ is $(CH_2)_m$—N=B wherein N=B is 4-morpholinyl, 4-thiomorpholinyl, 4-piperazinyl, 1-pyrrolidinyl or 1-piperidinyl, each of which may be substituted or unsubstituted.

9. A compound selected from the group consisting of:
3-(3-Benzyl-[1,2,4]-oxadiazol-5-yl)-1-[2-(pyrrolidin-1-yl)ethyl]-1H-indole,
3-(3-Benzyl-[1,2,4]-oxadiazol-5-yl)-1-[2-(morpholin-4-yl)ethyl]-1H-indole,
3-(3-Phenyl-[1,2,4]-oxadiazol-5-yl)-1-[2-(morpholin-4-yl)ethyl]-1H-indole,
1-[2-(Morpholin-4-yl)ethyl]-3-(3-thien-2-ylmethyl-[1,2,4]oxadiazol-5-yl)-1H-indole,
3-(3-Benzyl-[1,2,4]oxadiazol-5-yl)-1-[2-(piperidin-1-yl)ethyl]-1H-indole,
3-[3-(4-Methoxy-benzyl)-[1,2,4]oxadiazol-5-yl]-1-[2-(morpholin-4-yl)ethyl]-1H-indole,
3-[3-(4-Bromo-benzyl)-[1,2,4]oxadiazol-5-yl]-1-[2-(morpholin-4-yl)ethyl]-1H-indole,
1-[2-(morpholin-4-yl)ethyl]-3-(3-phenethyl-[1,2,4] oxadiazol-5-yl)-1H-indole,
3-[3-(2-Chlorobenzyl)-[1,2,4]-oxadiazol-5-yl]-1-[2-(morpholin-4-yl)ethyl]-1H-indole,
3-[3-(Biphenyl)-[1,2,4]oxadiazole-5-yl]-1-[2-(morpholin-4-yl)ethyl]-1H-indole,
3-[3-(Naphth-2-ylmethyl)-[1,2,4]-oxadiazol-5-yl]-1-[2-(pyrolidin-1-yl)ethyl]-1H-indole,
3-[3-(Naphth-2-ylmethyl)-[1,2,4]-oxadiazol-5-yl]-1-[2-(morpholin-4-yl)ethyl]-1H-indole,
Ethyl 5-([3-(naphth-2-ylmethyl)-[1,2,4]-oxadiazole-5-yl]-1H-indol-1-yl)pentanoate 5-([3-(Naphth-2-ylmethyl)-[1,2,4]-oxadiazole-5-yl]-1H-indol-1-yl)pentanoic acid, and Ethyl 3-([3-(Naphth-2-ylmethyl)-1,2,4-oxadiazol-5-yl]-1H-indol-1-yl)propanoate.

10. 3-(3-Benzyl-[1,2,4]-oxadiazol-5-yl)-1-[2-(pyrrolidin-1-yl)ethyl]-1H-indole, or pharmaceutically acceptable salt or prodrug thereof.

11. A salt of a compound of any one of claim 1, 9 or 10 wherein the salt is a tartrate salt.

12. A composition comprising a compound according to claim 1, or a pharmaceutically acceptable salt or prodrug thereof, together with a pharmaceutically acceptable additive.

13. A composition according to claim 12 wherein the compound is 3-(3-Benzyl-[1,2,4]-oxadiazol-5-yl)-1-[2-(pyrrolidin-1-yl)ethyl]-1H-indole, or pharmaceutically acceptable salt or prodrug thereof.

14. A method for modulating the activity of a cannabinoid receptor in a subject in need thereof comprising administering to said subject a modulating effective amount of a compound of Formula (I):

(I)

wherein n is 0, 1 or 2:

$R_1$ is either:

a monocyclic group selected from the group consisting of 2-thienyl, 3-thienyl, 2-furanyl, 3-furanyl, 2-pyrrolyl, and 3-pyrrolyl, each of which may be unsubstituted or substituted 1 to 3 times by a substituent; styryl, or phenyl, each of which may be unsubstituted or substituted 1 to 4 times by a substituent; or phenyl or styryl, each substituted by methylenedioxy; or a polycyclic group selected from the group consisting of 1-naphthyl, 2-naphthyl, 2-biphenyl, 4-biphenyl, (1H-imidazol-1-yl)napththyl, 2-(1-naphthyl)ethenyl, 1-(1,2,3,4-tetrahydronaphthyl), anthryl, phenanthryl, pyrenyl, benzo[b]furyl, benzothienyl, indolyl, quinolyl, isoquinolyl, and 1H-benzimidazolyl, each of which may be unsubstituted or substituted 1 to 4 times by a substituent;

wherein said substituents are independently selected from the group consisting of halogen, lower alkyl, lower alkoxy, hydroxy, nitro, cyano, amino, N-lower alkylamino, N,N-di-lower alkylamino, lower alkylthio, mercapto, lower alkylsulphinyl, lower alkylsulphonyl, and trifluoromethyl;

$R_2$ is hydrogen, lower alkyl or halo;

p is 0, 1, 2 or 3;

each $R_3$ is independently selected from the group consisting of hydroxy, lower alkyl, lower alkoxy, halogen, mercapto, lower alkylthio, amino, N-lower alkylamino, N,N-di-lower alkylamino, nitro, trifluoromethyl and trifluoromethoxy;

when $R_5$ is $(CH_2)_m$-Het, $(CH_2)_m$—N=B or $(CH_2)_q$-Z, $R_4$ is selected from the group consisting of hydrogen, lower alkyl, lower alkoxy, halogen, mercapto, lower alkylthio, amino, N-lower alkylamino, N,N-di-lower alkylamino, nitro, trifluoromethyl and trifluoromethoxy; or when $R_5$ is $CHR_6CH_2$—N=B or $CHR_6CH_2$-Het, $R_4$ and $R_6$ together form a group —Y—$CH_2$— wherein Y is O or $CH_2$ and is bonded to the 7-position of the indole ring; or when $R_5$ is $CH_2CHR_8CH_2$—N=B or $CH_2CHR_8CH_2$-Het, $R_4$ and $R_8$ together form —O— or —$CH_2$—;

$R_5$ is selected from the group consisting of $(CH_2)_m$-Het, $(CH_2)_m$—N=B, $(CH_2)_q$-Z, $CHR_6CH_2$—N=B, $CHR_6CH_2$-Het, $CH_2CHR_8$—N=B and $CH_2CHR_8CH_2$-Het;

wherein m is 0, 1, 2, 3 or 4 and when m is not 0, a $CH_2$ group of the alkyl chain $(CH_2)_m$ may be substituted by lower alkyl; and q is 1, 2, 3 or 4, wherein a $CH_2$ group of the alkyl chain $(CH_2)_q$ may be substituted by lower alkyl;

Het is a heterocycle, attached at a carbon atom, selected from the group consisting of: 2-pyrrolidinyl, 3-pyrrolidinyl, 2-piperidinyl, 3-piperidinyl, 4-piperidinyl, 2-morpholinyl, 3-morpholinyl, 2-thiomorpholinyl or 5-oxide thereof, 3-thiomorpholinyl or 5-oxide thereof, 2-piperazinyl, tetrahydropuridinyl, azetidinyl, 2-, 3- or 4-hexahydroazepinyl, 2-, 3- or 4-hexahydro thiazepinyl, 2-indolinyl, 3-indolinyl, 1-isoindolinyl, 2-pyrrolyl, 3-pyrrolyl, 2-pyridinyl, 3-pyridinyl, 4-pyridinyl, 2-pyrazinyl, 2-pyrimidinyl and 4-pyrimidinyl;

wherein the carbon atoms of said heterocycle may be unsubstituted or 1, 2 or 3 carbon atoms may be independently substituted by oxo, hydroxy, lower alkyl or lower alkoxy; and the nitrogen atom of said heterocycle may be unsubstituted or substituted by lower alkyl, benzyl, lower alkylbenzyl, lower alkoxylbenzyl, halobenzyl, or benzhydryl;

—N=B is N,N-di-lower alkylamino, or a heterocycle selected from the group consisting of 4-morpholinyl, 4-thiomorpholinyl, 4-piperazinyl, 1-pyrrolidinyl, or 1-piperidinyl wherein the carbon atoms of said heterocycle may be unsubstituted or 1, 2 or 3 carbon atoms may be independently substituted by hydroxy, lower alkyl or lower alkoxy; and Z is methyl, halogen or $CO_2R_7$ wherein $R_7$ is lower alkyl or hydrogen;

or a pharmaceutically acceptable salt or prodrug thereof.

15. A method for treating a disease or condition in a subject, wherein the disease or condition is, comprising administering to said subject a treatment effective amount of a compound of Formula (I):

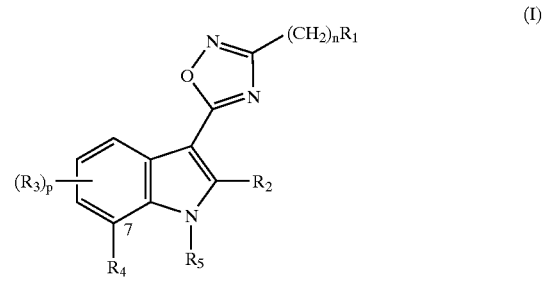

wherein n is 0, 1 or 2;

$R_1$ is either:

a monocyclic group selected from the group consisting of 2-thienyl, 3-thienyl, 2-furanyl, 3-furanyl, 2-pyrrolyl, and 3-pyrrolyl, each of which may be unsubstituted or substituted 1 to 3 times by a substituent; styryl, or phenyl, each of which may be unsubstituted or substituted 1 to 4 times by a substituent; or phenyl or styryl, each substituted by methylenedioxy; or a polycyclic group selected from the group consisting of 1-naphthyl, 2-naphthyl, 2-biphenyl, 4-biphenyl, (1H-imidazol-1-yl)napththyl, 2-(1-naphthyl)ethenyl, 1-(1,2,3,4-tetrahydronaphthyl), anthryl, phenanthryl, pyrenyl, benzo[b]furyl, benzothienyl, indolyl, quinolyl, isoquinolyl, and 1H-benzimidazolyl, each of which may be unsubstituted or substituted 1 to 4 times by a substituent;

wherein said substituents are independently selected from the group consisting of halogen, lower alkyl, lower alkoxy, hydroxy, nitro, cyano, amino, N-lower alkylamino, N,N-di-lower alkylamino, lower alkylthio, mercapto, lower alkylsulphinyl, lower alkylsulphonyl, and trifluoromethyl;

$R_2$ is hydrogen, lower alkyl or halo;

p is 0, 1, 2 or 3;

each $R_3$ is independently selected from the group consisting of hydroxy, lower alkyl, lower alkoxy, halogen, mercapto, lower alkylthio, amino, N-lower alkylamino, N,N-di-lower alkylamino, nitro, trifluoromethyl and trifluoromethoxy;

when $R_5$ is $(CH_2)_m$-Het, $(CH_2)_m$—N=B or $(CH_2)_q$-Z, $R_4$ is selected from the group consisting of hydrogen, lower alkyl, lower alkoxy, halogen, mercapto, lower alkylthio, amino, N-lower alkylamino, N,N-di-lower alkylamino, nitro, trifluoromethyl and trifluoromethoxy; or when $R_5$ is $CHR_6CH_2$—N=B or $CHR_6CH_2$-Het, $R_4$ and $R_6$ together form a group —Y—$CH_2$— wherein Y is O or $CH_2$ and is bonded to the 7-position of the indole ring; or when $R_5$ is $CH_2CHR_8CH_2$—N=B or $CH_2CHR_8CH_2$-Het, $R_4$ and $R_8$ together form —O— or —$CH_2$—;

$R_5$ is selected from the group consisting of $(CH_2)_m$-Het, $(CH_2)_m$—N=B, $(CH_2)_q$-Z, $CHR_6CH_2$—N=B, $CHR_6CH_2$-Het, $CH_2CHR_8CH_2$—N=B and $CH_2CHR_8CH_2$-Het;

wherein m is 0, 1, 2, 3 or 4 and when m is not 0, a $CH_2$ group of the alkyl chain $(CH_2)_m$ may be substituted by lower alkyl; and q is 1, 2, 3 or 4, wherein a $CH_2$ group of the alkyl chain $(CH_2)_q$ may be substituted by lower alkyl;

Het is a heterocycle, attached at a carbon atom, selected from the group consisting of: 2-pyrrolidinyl, 3-pyrrolidinyl, 2-piperidinyl, 3-piperidinyl, 4-piperidinyl, 2-morpholinyl, 3-morpholinyl, 2-thiomorpholinyl or 5-oxide thereof, 3-thiomorpholinyl or 5-oxide thereof, 2-piperazinyl, tetrahydropuridinyl, azetidinyl, 2-, 3- or 4-hexahydroazepinyl, 2-, 3- or 4-hexahydro thiazepinyl, 2-indolinyl, 3-indolinyl, 1-isoindolinyl, 2-pyrrolyl, 3-pyrrolyl, 2-pyridinyl, 3-pyridinyl, 4-pyridinyl, 2-pyrazinyl, 2-pyrimidinyl and 4-pyrimidinyl;

wherein the carbon atoms of said heterocycle may be unsubstituted or 1, 2 or 3 carbon atoms may be independently substituted by oxo, hydroxy, lower alkyl or lower alkoxy; and the nitrogen atom of said heterocycle may be unsubstituted or substituted by lower alkyl, benzyl, lower alkylbenzyl, lower alkoxylbenzyl, halobenzyl, or benzhydryl;

—N=B is N,N-di-lower alkylamino, or a heterocycle selected from the group consisting of 4-morpholinyl, 4-thiomorpholinyl, 4-piperazinyl, 1-pyrrolidinyl, or 1-piperidinyl wherein the carbon atoms of said heterocycle may be unsubstituted or 1, 2 or 3 carbon atoms may be independently substituted by hydroxy, lower alkyl or lower alkoxy; and Z is methyl, halogen or $CO_2R_7$ wherein $R_7$ is lower alkyl or hydrogen;

or a pharmaceutically acceptable salt thereof.

16. A method according to claim 15 wherein the pain is neuropathic pain.

17. A method according to claim 16 wherein the compound of Formula (I) is 3-(3-Benzyl-[1,2,4]-oxadiazol-5-yl)-1-[2-(pyrrolidin-1-yl)ethyl]-1H-indole, or pharmaceutically acceptable salt or prodrug thereof.

* * * * *

UNITED STATES PATENT AND TRADEMARK OFFICE
CERTIFICATE OF CORRECTION

PATENT NO.   : 6,930,118 B2
DATED        : August 16, 2005
INVENTOR(S)  : Peter Gerard Moloney et al.

Page 1 of 1

It is certified that error appears in the above-identified patent and that said Letters Patent is hereby corrected as shown below:

<u>Column 26,</u>
Line 8, "claim" should read -- claims --.

<u>Column 27,</u>
Line 22, "$CH_2CHR_8-N=B$" should read -- $CH_2CHR_8CH_2-N=B$ --.
Line 65, "is" should read -- is pain, --.

Signed and Sealed this

Eighteenth Day of April, 2006

JON W. DUDAS
*Director of the United States Patent and Trademark Office*